US009149308B2

(12) United States Patent
Biedermann et al.

(10) Patent No.: US 9,149,308 B2
(45) Date of Patent: Oct. 6, 2015

(54) TOOL FOR USE WITH A BONE ANCHOR, IN PARTICULAR FOR SPINAL SURGERY

(75) Inventors: Lutz Biedermann, VS-Villingen (DE); Wilfried Matthis, Weisweil (DE); Michael Kegel, Tennenbronn (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 644 days.

(21) Appl. No.: 12/755,360

(22) Filed: Apr. 6, 2010

(65) Prior Publication Data

US 2011/0004222 A1 Jan. 6, 2011

Related U.S. Application Data

(60) Provisional application No. 61/167,744, filed on Apr. 8, 2009.

(30) Foreign Application Priority Data

Apr. 7, 2009 (EP) .................................... 09005130

(51) Int. Cl.
*A61B 17/58* (2006.01)
*A61B 17/70* (2006.01)
(Continued)

(52) U.S. Cl.
CPC ......... *A61B 17/7091* (2013.01); *A61B 17/7082* (2013.01); *A61B 17/8875* (2013.01); *A61B 2019/301* (2013.01); *A61B 2019/464* (2013.01); *B25B 17/00* (2013.01)

(58) Field of Classification Search
CPC . B25B 17/00; A61B 17/8875; A61B 17/7082

USPC ................ 606/53, 61, 99, 104, 301; 81/57.29
See application file for complete search history.

(56) References Cited

U.S. PATENT DOCUMENTS 4,762,031 A * 8/1988 Bradley ....................... 81/57.22
5,734,113 A * 3/1998 Vogt et al. ................... 73/862.23
(Continued)

FOREIGN PATENT DOCUMENTS

DE 85 26 564 U1 3/1986
EP 1 726 264 A1 11/2006
(Continued)

OTHER PUBLICATIONS

Partial European Search Report for Application No. EP09005130, dated Sep. 25, 2009.
(Continued)

*Primary Examiner* — Eduardo C Robert
*Assistant Examiner* — Stuart S Bray
(74) *Attorney, Agent, or Firm* — Christie, Parker & Hale, LLP

(57) ABSTRACT

A tool is provided for use with a bone anchor, wherein the bone anchor has an anchoring section and a receiving portion for receiving a rod to be connected to the anchoring section and a locking element, the tool comprising a tip portion for engaging the locking element; a mechanism to apply torque to the tip portion comprising a drive shaft and a driven shaft coupled by a gear unit, where the drive shaft has a different axis than the driven shaft, and where the driven shaft comprises an engagement portion configured to connect the driven shaft to the gear unit; and a counter-holding portion for engaging the receiving part, wherein the counter-holding portion is rotatable with respect to the tip portion.

23 Claims, 10 Drawing Sheets

(51) Int. Cl.
*A61B 17/88* (2006.01)
*B25B 17/00* (2006.01)
*A61B 19/00* (2006.01)

(56) References Cited

U.S. PATENT DOCUMENTS

| | | | |
|---|---|---|---|
| 6,272,952 B1* | 8/2001 | Hsu et al. | 81/57.22 |
| 6,330,845 B1* | 12/2001 | Meulink | 81/462 |
| 6,379,361 B1* | 4/2002 | Beck et al. | 606/323 |
| 6,393,949 B1* | 5/2002 | Ho | 81/62 |
| 6,634,260 B1* | 10/2003 | Smith | 81/57.36 |
| 6,723,100 B2* | 4/2004 | Biedermann et al. | 606/308 |
| 7,097,648 B1* | 8/2006 | Globerman et al. | 606/99 |
| 7,100,476 B1* | 9/2006 | Feit | 81/57.29 |
| 7,296,500 B1* | 11/2007 | Martinelli | 81/57.29 |
| 7,338,499 B1* | 3/2008 | Kuczynski et al. | 606/102 |
| 7,363,838 B2* | 4/2008 | Abdelgany | 81/60 |
| 7,588,573 B2* | 9/2009 | Berry | 606/86 A |
| 7,608,078 B2* | 10/2009 | Berry | 606/86 A |
| 8,267,998 B2* | 9/2012 | Kraus | 623/17.11 |
| 2003/0213340 A1* | 11/2003 | Alden | 81/57.29 |
| 2004/0187651 A1* | 9/2004 | Amami | 81/467 |
| 2004/0267275 A1* | 12/2004 | Cournoyer et al. | 606/99 |
| 2004/0267373 A1* | 12/2004 | Dwyer et al. | 623/22.12 |
| 2005/0033292 A1* | 2/2005 | Teitelbaum et al. | 606/53 |
| 2005/0256525 A1* | 11/2005 | Culbert et al. | 606/53 |
| 2006/0089644 A1* | 4/2006 | Felix | 606/61 |
| 2006/0111712 A1* | 5/2006 | Jackson | 606/61 |
| 2007/0006692 A1* | 1/2007 | Phan | 81/475 |
| 2007/0149981 A1* | 6/2007 | Bhattacharyya | 606/99 |
| 2007/0175956 A1 | 8/2007 | Swayze et al. | |
| 2007/0175960 A1 | 8/2007 | Shelton, IV et al. | |
| 2008/0154278 A1* | 6/2008 | Abdelgany | 606/99 |
| 2008/0200918 A1* | 8/2008 | Spitler et al. | 606/104 |
| 2008/0243134 A1* | 10/2008 | Limberg et al. | 606/104 |
| 2008/0281336 A1* | 11/2008 | Zergiebel | 606/142 |
| 2009/0024174 A1* | 1/2009 | Stark | 606/321 |
| 2009/0112219 A1* | 4/2009 | Daniels et al. | 606/99 |
| 2009/0222019 A1* | 9/2009 | Bhattacharyya | 606/99 |
| 2009/0275954 A1* | 11/2009 | Phan et al. | 606/104 |
| 2010/0030278 A1* | 2/2010 | Hawkes et al. | 606/301 |
| 2010/0100101 A1* | 4/2010 | Kraus | 606/99 |
| 2010/0211115 A1* | 8/2010 | Tyber et al. | 606/305 |
| 2011/0004222 A1* | 1/2011 | Biedermann et al. | 606/104 |
| 2011/0257656 A1* | 10/2011 | Daniels et al. | 606/99 |

FOREIGN PATENT DOCUMENTS

| | | |
|---|---|---|
| JP | 2003-19142 A | 1/2003 |
| JP | 2003-52710 A | 2/2003 |
| JP | 2005-503859 A | 2/2005 |
| JP | 2008-532705 A | 8/2008 |
| KR | 10-2007-0079049 A | 8/2007 |
| KR | 10-2007-0079050 A | 8/2007 |
| WO | WO 03/026513 A1 | 4/2003 |
| WO | WO 2006/101898 A1 | 9/2006 |

OTHER PUBLICATIONS

English translation of Japanese Office Action for Application No. 2010-086298, mailed Oct. 29, 2013, 7 pages.

\* cited by examiner

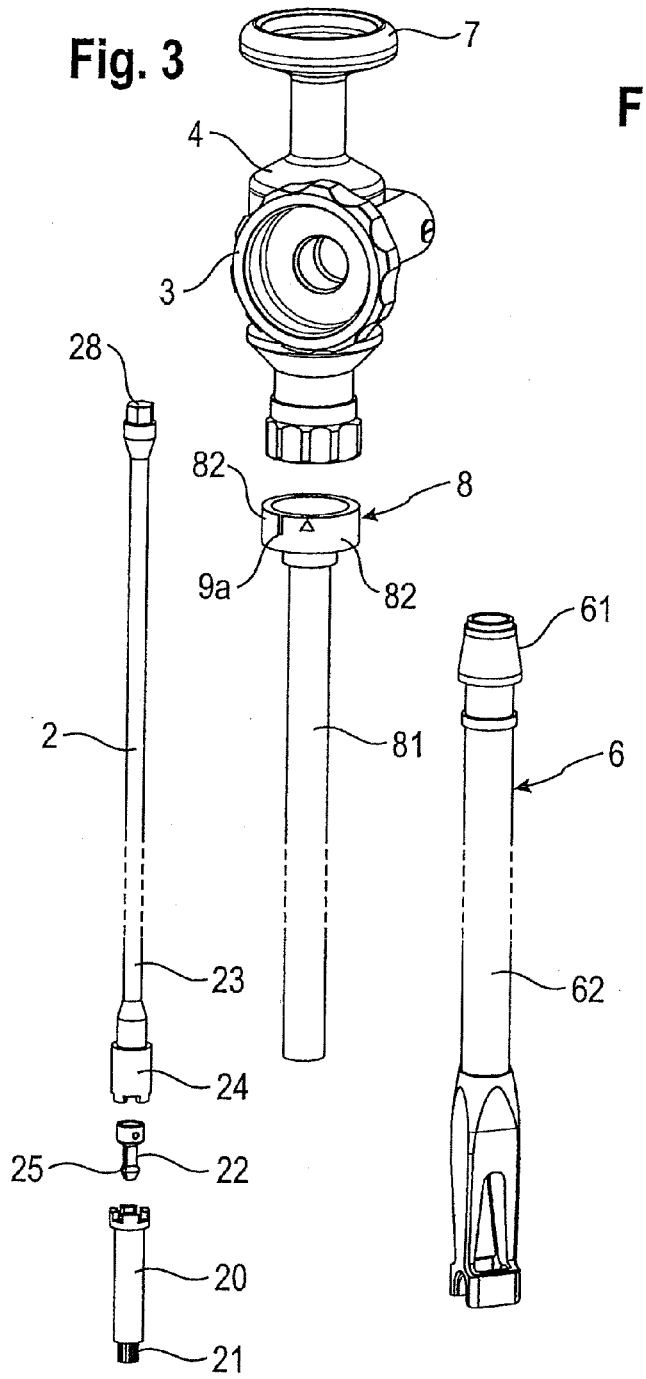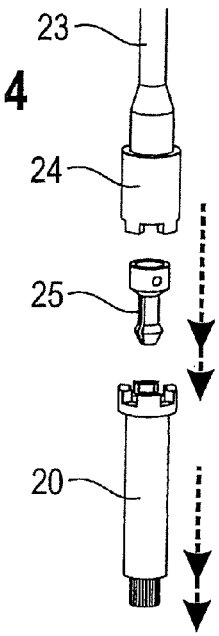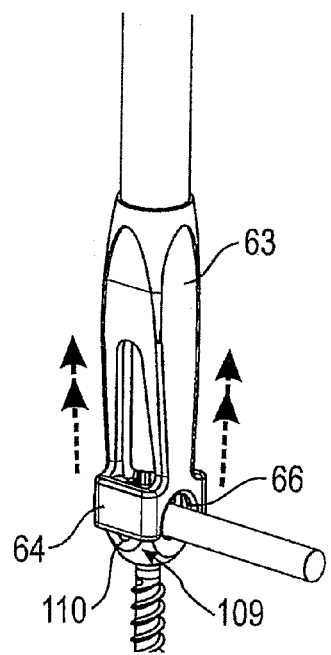

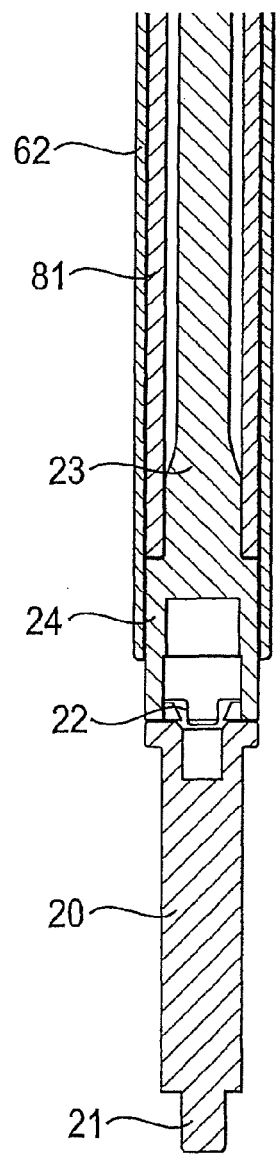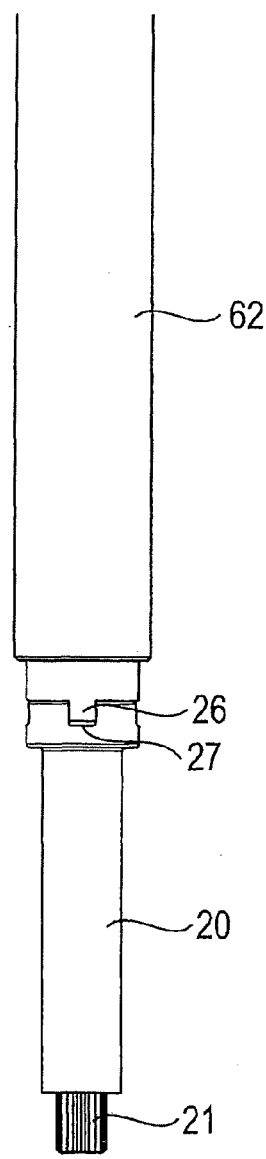

Fig. 8
Fig. 9
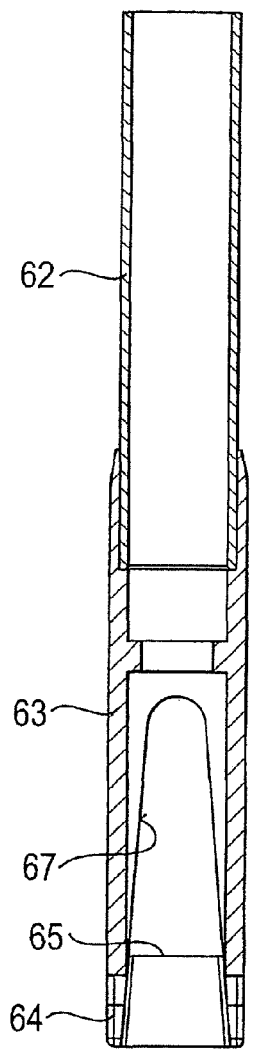
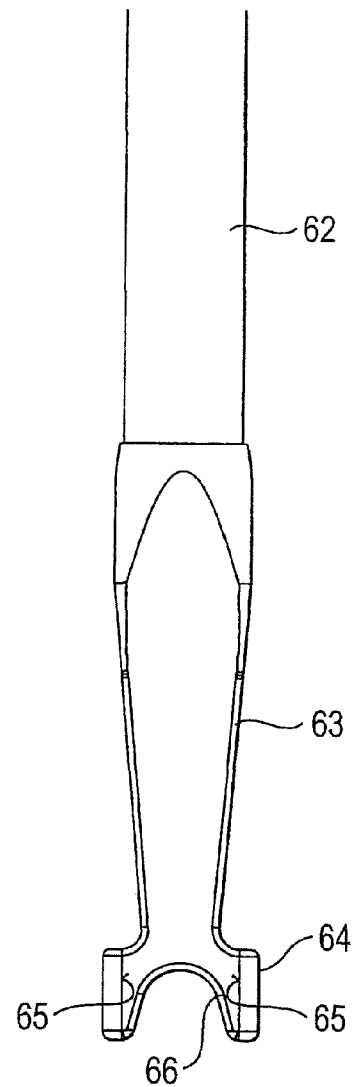

Fig. 15
Fig. 16
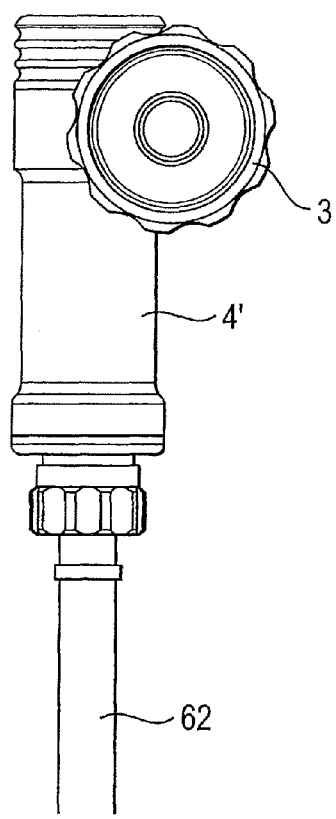
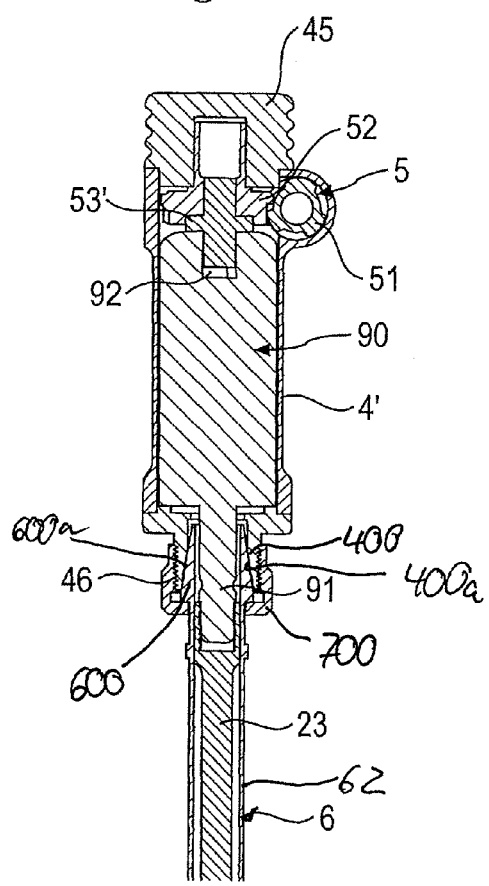

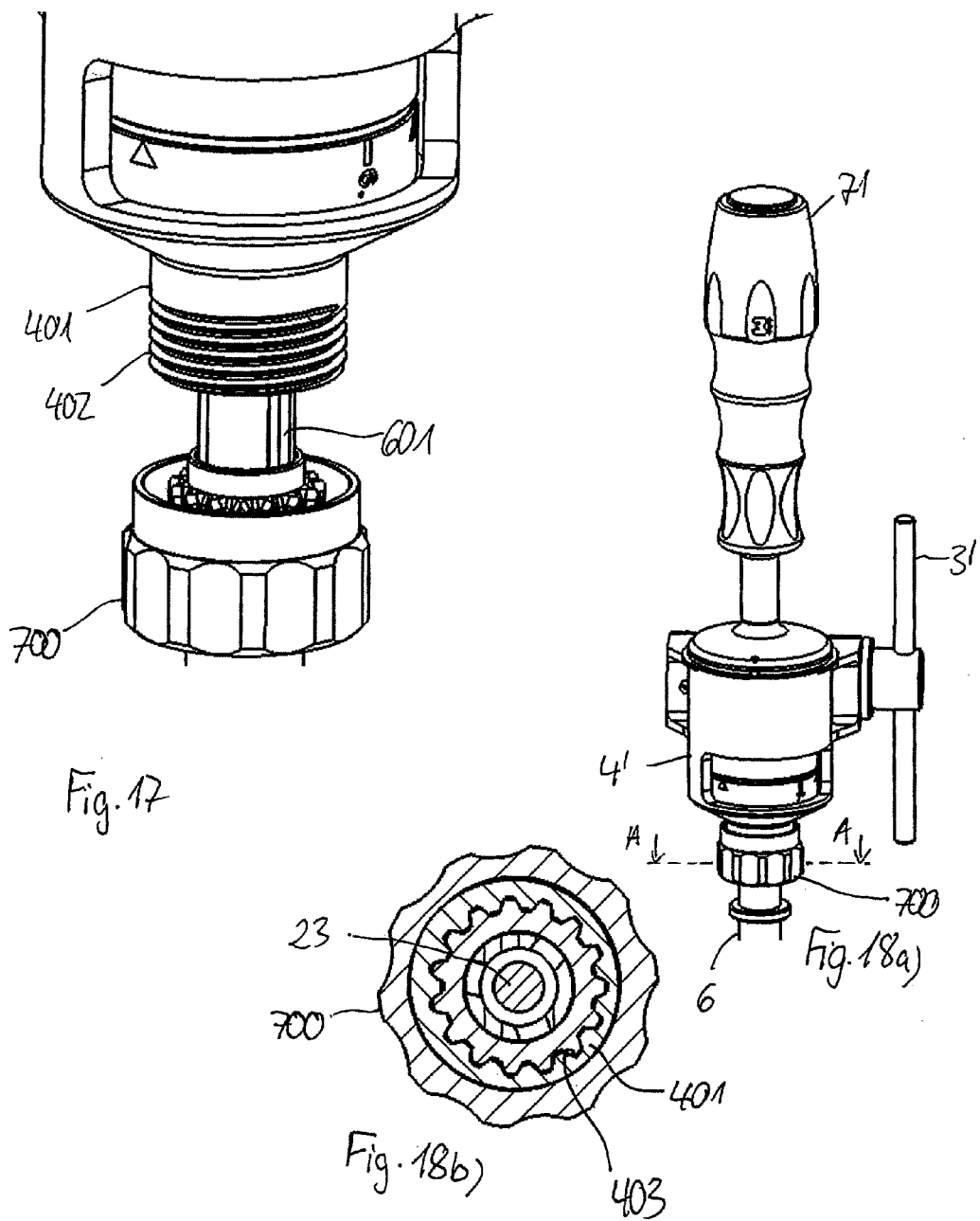

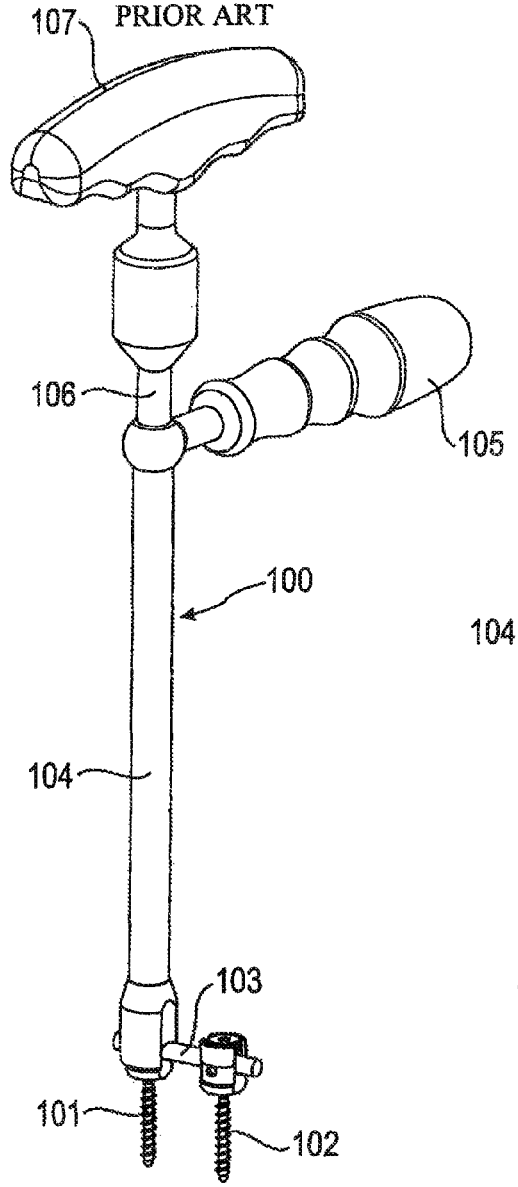
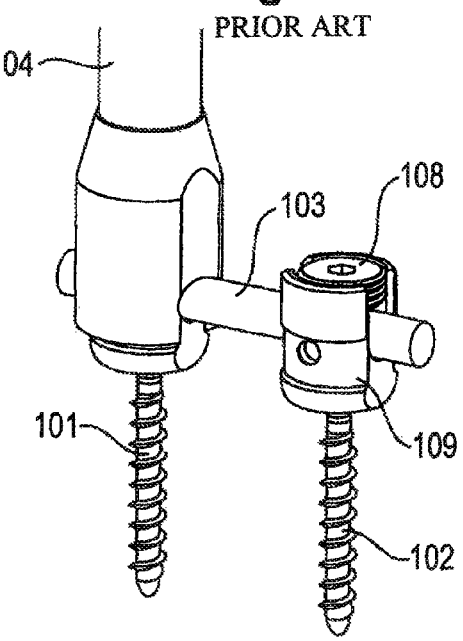

TOOL FOR USE WITH A BONE ANCHOR, IN PARTICULAR FOR SPINAL SURGERY

CROSS-REFERENCE TO RELATED APPLICATION(S)

This application claims priority to and the benefit of European Patent Application No. 09 005 130.1 filed in the European Patent Office on Apr. 7, 2009, the entire content of which is incorporated herein by reference. This application also claims priority to and the benefit of U.S. Provisional Application No. 61/167,744 filed in the US Patent and Trademark Office on Apr. 8, 2009, the entire content of which is incorporated herein by reference.

BACKGROUND

The invention relates to a tool for use with a bone anchor. The bone anchor includes an anchoring section and a receiving part for receiving a rod to be connected to the anchoring section and a locking element. The tool is particularly applicable in spinal surgery, for example for the fixation of a rod to pedicle screws.

A known tool 100 is shown in FIGS. 19 and 20 in connection with polyaxial screws 101 and 102, which are connected via a rod 103. The tool 100 includes a counter-holding portion 104 with a handle 105 and a screw driver portion 106. The screw driver portion 106 is rotatable with respect to the counter-holding portion 104 and also comprises a handle 107. The screw driver portion 106 has a tip portion (not shown) that engages a locking screw 108 of the polyaxial screw 101 for fixation of the rod 103 within the receiving portion 109. The counter-holding portion 104 engages the receiving portion 109 and holds the receiving portion during tightening of the locking screw 108. The tightening torque which is necessary for finally tightening the locking screw 108 is typically in the range of approximately 7 to 15 Nm. The counter-holding portion 104 is advantageous in particular for counter-holding such high tightening torques. However, since the counter-holding portion acts at least partially onto the rod, the known tool is not suitable for flexible rods, for example for rods made of an elastomer material such as polycarbonate urethane (PCU), since the loads would lead to deformations which may damage the rod. Further, sensitive handling with two hands is difficult when applying high tightening torques.

A tool which has a counter-holding portion that engages the receiving portion of a bone anchor in a positive fit manner is known from European Patent Application EP 1 726 264.

SUMMARY

An embodiment of the invention is a tool for use with a bone anchor of the above described type where loads acting onto the bone anchor and therefore onto the bone are reduced and which may allow for a facilitated handling.

An embodiment of the tool includes a tip portion for engaging a locking element of a bone anchor; a mechanism to apply torque to the tip portion, wherein the mechanism to apply torque includes a drive shaft and a driven shaft coupled by a gear unit, and wherein the drive shaft has a different axis than the driven shaft; and a counter-holding portion, wherein the tip portion is rotatable with respect to the counter-holding portion.

A feature of the tool is that the tightening torque which has to be applied manually by the surgeon is considerably reduced. Therefore, the manually-applied fastening torque is small and tightening of the locking screw can be performed smoothly.

The flow of forces is restricted to the locking element and the tool, which implies that the force applied during a final tightening is transferred directly from the locking element through the receiving member to the counter-holding portion. This results in an unloaded rod element. In addition, the tightening load is not transferred into the bone by the bone anchor.

The tip portion of the screw driver portion of the tool may be exchangeable. Therefore, a suitable tip portion can be selected and the tool can be used for different kinds of locking elements.

The applied fastening torque may be limited either by observing a display indicating the applied torque and manually stopping the application of torque or by using a preset torque adapter that can be mounted together with the gear unit.

Principles and further features of the present invention will become apparent by a detailed description of embodiments and by means of the accompanying drawings.

BRIEF DESCRIPTION OF THE DRAWINGS

FIG. 3 shows a perspective exploded view of the tool.
FIG. 4 shows an enlarged portion of FIG. 3 with arrows indicating the torque flow.
FIG. 5 shows a further enlarged portion of FIG. 3 with arrows showing the torque flow.
FIG. 6 shows a sectional view of a lower portion of the driven shaft of the tool.
FIG. 7 shows a side view of the lower portion of the driven shaft according to FIG. 6.
FIG. 8 shows a sectional view of the lower portion of the counter-holding portion of the tool.
FIG. 9 shows a side view of the counter-holding portion according to FIG. 8.
FIG. 15 shows a schematic side view of the upper portion of a further embodiment of the tool.
FIG. 16 shows a schematic sectional view of the further embodiment shown in FIG. 15.
FIG. 17 shows a perspective view of a portion of a still further embodiment of the tool in a not fully mounted condition.
FIG. 18a shows a perspective view of a greater portion of the still further embodiment of FIG. 17 in a mounted condition.
FIG. 18b shows an enlarged cross-sectional view along line A-A shown in FIG. 18a
FIG. 19 shows a perspective view of a known tool.
FIG. 20 shows an enlarged portion of FIG. 19.

DETAILED DESCRIPTION

Figure 1:
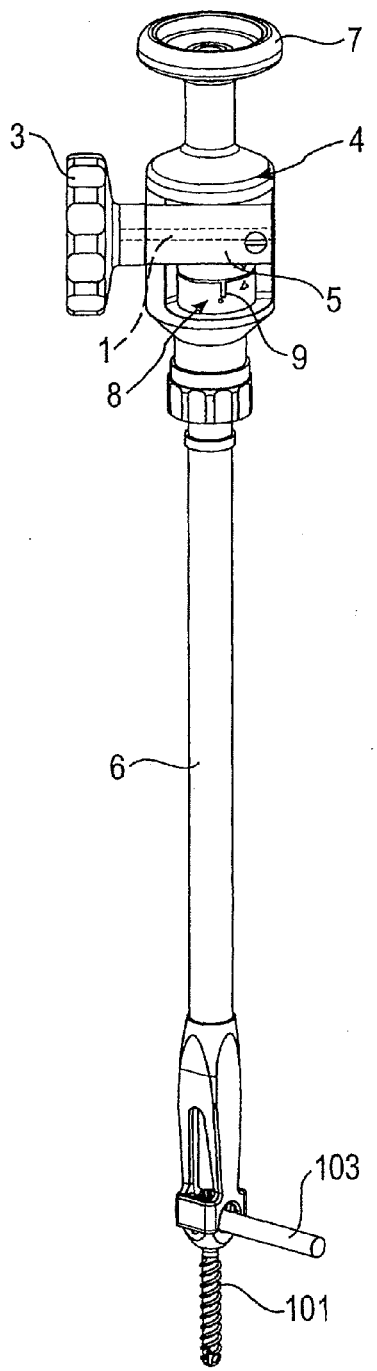
FIG. 1 shows a perspective view of an embodiment of the tool.

With reference to FIGS. 1 to 5, a tool according to one embodiment comprises a screw driver portion, which includes a drive shaft 1 as schematically shown by the dashed line in FIG. 1 and a driven shaft 2 as shown in FIG. 3. The drive shaft 1 has a handle 3 at its free end projecting outside a housing 4. The drive shaft 1 and the driven shaft 2 enclose an angle of 90° and are connected by a reduction gear unit 5, which will be explained in more detail below.

The tool further comprises a counter-holding portion 6, which is fixedly connected to the housing 4 so that the driven shaft 2 is rotatable with respect to the counter-holding portion 6. At its free end opposite to the counter-holding portion 6, the housing 4 comprises a handle 7 for holding the tool. The central axis of the handle 7 extends substantially perpendicular to the central axis of the handle 3 of the drive shaft 1. This allows a convenient handling of the counter-holding portion.

The tool further has a display member 8, which may include visual marks 9 for indicating the applied torque. The driven shaft 2 has, as can be seen in FIGS. 3, 4, 6 and 7, a tip portion 20 with an engagement portion 21 for engagement with a locking element of a bone anchor. Such a locking element can be, for example, a set screw 108 (shown in FIG. 18) of a receiving portion 109 of a polyaxial bone screw 102. The engagement portion 21 can have a hexagon shape or a flathead, crosshead, square, hex socket or Torx® shape, or any other shape adapted to the respective engagement portion of the locking element. The tip portion is connected via a plug connection member 22 to a main shaft portion 23 of the driven shaft 2. The main shaft portion 23 has, at its end facing the tip portion 20, a section 24 with an enlarged outer diameter and a recess for inserting the plug connection member 22. The tip portion 20 has, at its end facing the main shaft portion 23, a recess for inserting a portion of the plug connection member 22. The plug connection member 22 may have a resilient portion 25, which allows for the releasable holding of the tip portion 20 in the main shaft portion 23. Further, the tip portion 20 and the main shaft portion 23 are connected in a positive fit manner, such as, for example, shown in FIG. 7 by means of circumferentially-projecting portions 26 which engage in circumferentially-arranged recesses 27 at the corresponding other part.

A plurality of tip portions 20 may be provided with different engagement portions 21, which can be interchangeably connected to the main shaft portion 23. By means of the plug connection member 22, the exchange of the tip portion 20 can be easily made by hand. At its end facing the gear unit 5, the main shaft portion 23 comprises an engagement portion 28 to be connected with the gear unit 5.

The drive shaft 1 and the reduction gear unit 5 are now explained with particular reference to FIGS. 3 and 10 to 13. In the embodiment shown, the gear unit 5 includes a worm drive having a worm 51 connected to the drive shaft 1 and a worm wheel 52. The worm wheel 52 also is provided with an engagement portion 53 to be engaged with the engagement portion 28 of the main shaft portion 23. A preferred gear transmission ratio for the application in spinal surgery is around 3:1 or 10:1. The worm drive is advantageous to transmit higher torques. A common feature of a worm drive is that the direction of transmission from the drive shaft to the driven shaft is not reversible. In surgery, this means that the final tightening of the locking element can be performed exactly.

As shown in FIGS. 3, 6 and 7, a display member 8 comprises a tube portion 81, which is fixed at its lower end to the main shaft portion 23 of the driven shaft 2 so that the tube portion 81 rotates with the driven shaft 2. At its end facing away from the tip portion 20, the display member 8 comprises a lower ring-shaped portion 82 with an enlarged diameter. The lower ring-shaped portion 82 carries a first visual mark 9a at its outer side. The visual mark 9a can be of any type including bars, engravings etc. It is configured to indicate a predefined tightening torque. The display member 8 further comprises an upper ring-shaped portion 83, which is connected to the worm wheel 52 and therefore to the main shaft portion 23 of the driven shaft 2. The lower ring-shaped portion 82 and the upper ring-shaped portion 83 are rotatable against each other. Between the two ring-shaped portions, a ring-shaped plate member for facilitating gliding may be provided. Both the upper and lower ring-shaped portions 83 and 82 have second visual marks 9b, which indicate a zero position.

Figure 10:
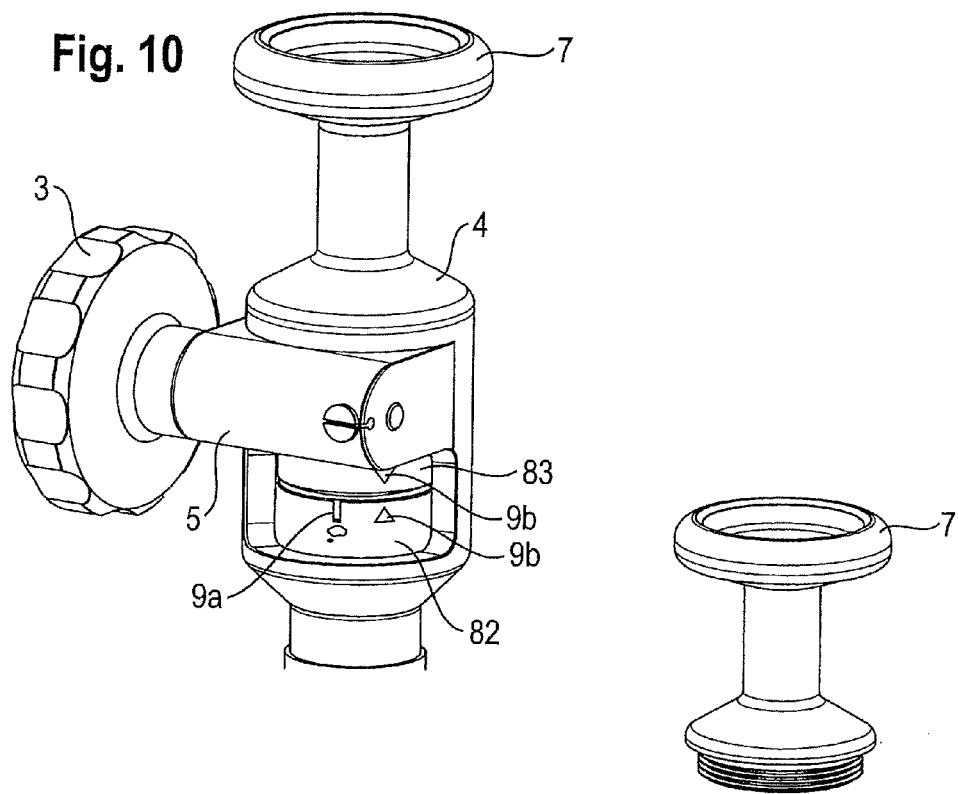
FIG. 10 shows an enlarged perspective view of an upper portion of the tool.
Figure 11:
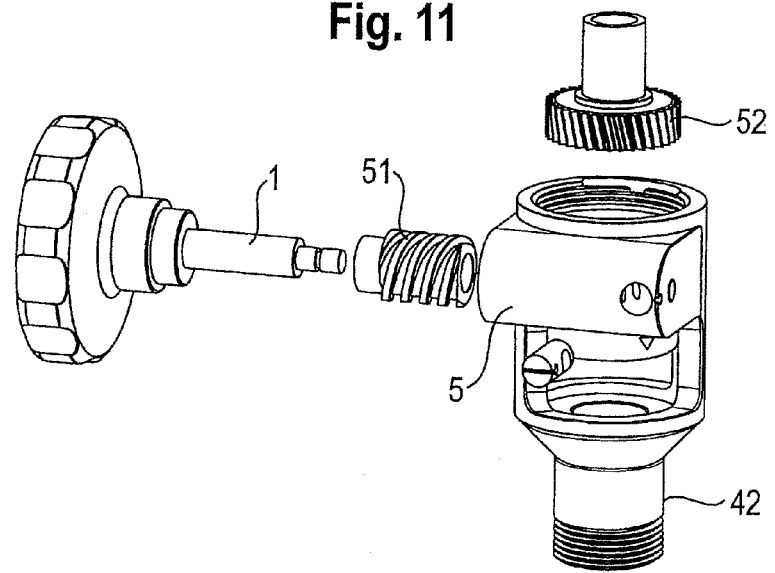
FIG. 11 shows an exploded perspective view of the upper portion of the tool including the drive shaft.
Figure 12:
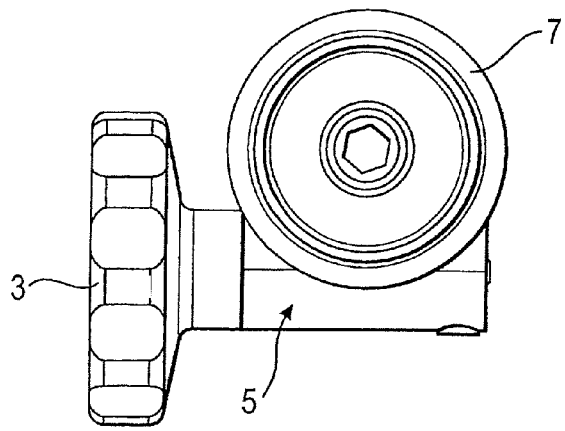
FIG. 12 shows a plan view of the tool.
Figure 13:
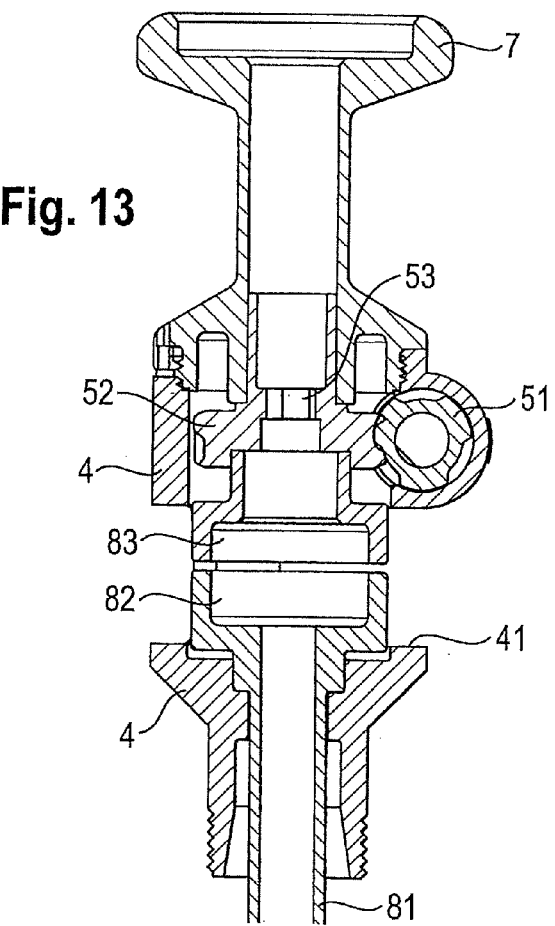
FIG. 13 shows a sectional view of the upper portion of the tool.

As can be seen in FIGS. 10 and 13, the housing 4 comprises a recess 41 to allow inspection of the visual marks 9a and 9b that indicate the applied torque.

With regard to FIG. 3, the handle 7 may be fixedly attached to the housing 4, for example by screwing as shown in FIG. 13. The housing 4 further has on its end opposite to the handle 7 a projection with fixation means, for example of the type of a thread, to connect the housing 4 to the counter-holding portion 6. The counter-holding portion 6 has on its end facing the housing 4 connection means 61 for connecting the counter-holding portion 6 fixedly to the housing 4. The counter-holding portion 6 further includes a main tube portion 62, shown in FIG. 3, the diameter of which is such that the driven shaft 2 and the tube portion 81 can be arranged and freely rotate therein. Further, the counter-holding portion 6 comprises an end section 63, as shown in FIGS. 3 and 5. The end section 63 is hollow so that the tip portion 20 extends through the end section 63. The end section 63 has at its free end an engagement portion 64. The engagement portion 64 is configured to engage the receiving portion 109 of the bone anchor. The engagement section 64 has a square or rectangular inner contour that is adapted to the outer contour of the receiving portion 109. In the embodiment shown, the receiving portion 109 has two opposed flat outer surfaces 110 as shown for example in FIG. 5. The engagement section 64 has inner flat surfaces 65 on two opposing sides, as shown in FIGS. 8 and 9, that are configured to correspond with the two flat outer surfaces 110 on the receiving portion 109. In addition, the engagement portion 64 has on each of the other two sides a recess 66 where the rod 103 can be guided through. The end section 63 further has on each of the sides that include the inner flat surface 65 a recess 67, which allows for visualization of the inserted tip portion 20.

In the embodiment shown, the end section 63 is fixedly connected to the end tube portion 62. However, the end section 63 may also be releasably attached thereto so as to allow fixation of different end sections 63 with an engagement portion 64 adapted to the shape and size of the receiving portions 109. Hence, the engagement portion 64 may have any shape that provides for a positive fit connection with the receiving portion 109 without acting onto the rod 103.

Figure 2:
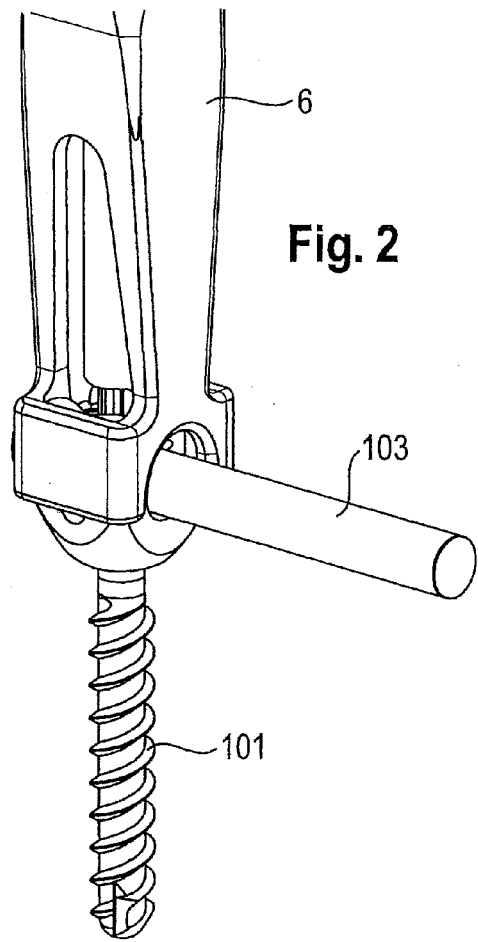
FIG. 2 shows an enlarged portion of FIG. 1.
Figure 14:
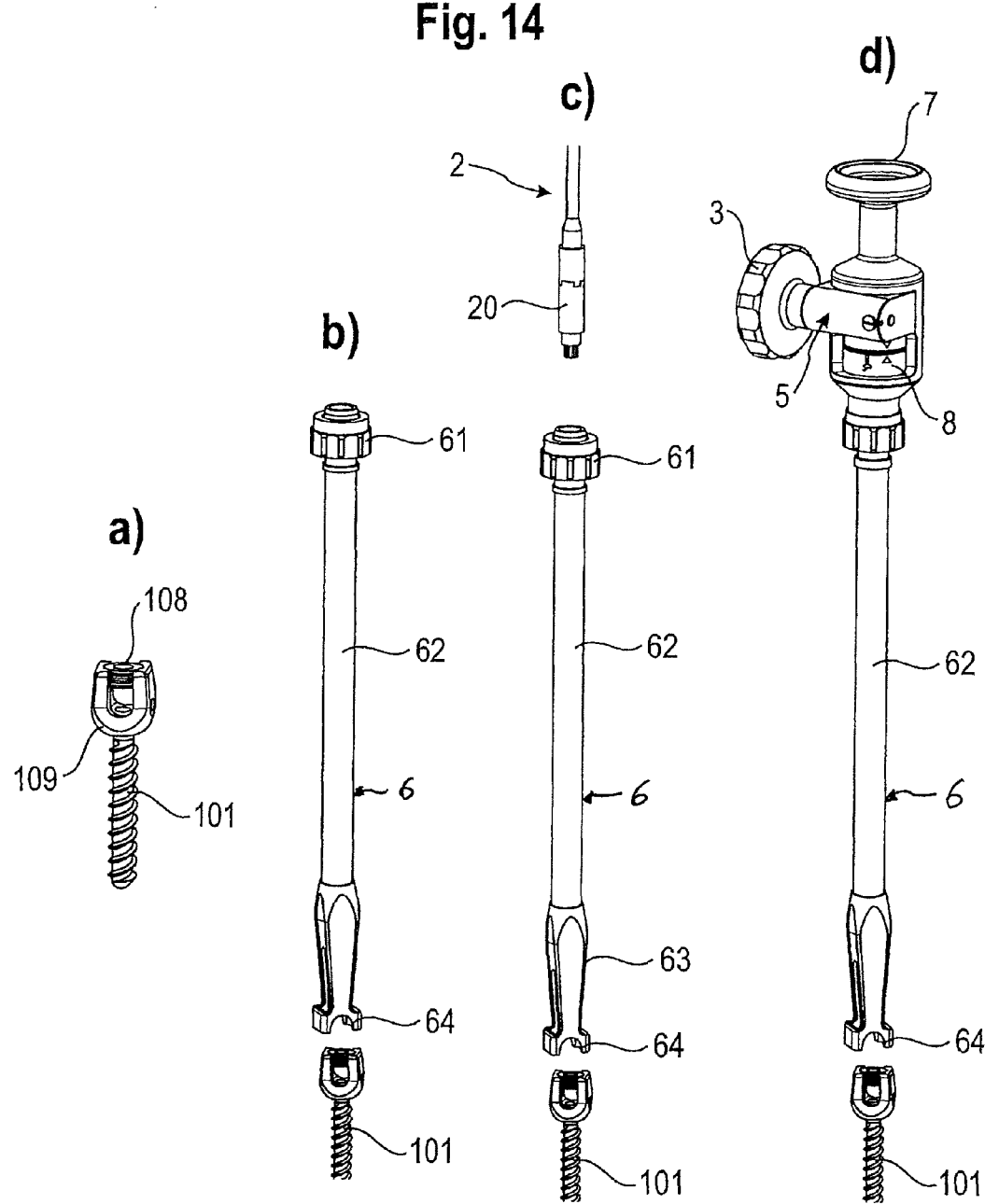
FIGS. 14a to d show steps of assembling and applying the tool.

Use of an embodiment of the tool is now explained with reference to FIGS. 14a to d. FIG. 14a schematically shows a bone anchor which is in this example a polyaxial bone screw 101 comprising a receiving portion 109 and a set screw 108 for fixation of the rod (not shown) in the receiving portion 109. The rod 103 is shown in FIG. 2. The bone anchor 101 is inserted into the bone, and then the rod 103 is inserted into the receiving portion 109. Thereafter the set screw 108 is inserted into the receiving portion 109. The engagement portion 64 of the counter-holding portion 6 of the tool engages the receiving portion 109 as shown in FIG. 14b. Thereafter, as shown in FIG. 14c, a driven shaft 2 including a tip portion 20 is inserted into the counter-holding portion 6. Next, as shown in FIG. 14d, a housing 4 with a handle 3, a reduction gear unit 5 and a handle 7 is mounted. In this condition, by rotating the drive shaft by means of the handle 3 the set screw is screwed in. When the set screw 108 abuts the rod and is blocked thereby and the drive shaft 1 is further rotated, the main shaft portion 23 of the driven shaft 2 becomes twisted by the torque which is introduced by the worm wheel 52 via the engagement portions 53 and 28. The upper ring-shaped portion 83, which is fixedly connected to the upper end of the main shaft portion 23, is rotated by the worm wheel 52 as long as the handle 3 is rotated by the surgeon. The lower ring-shaped portion 82 is connected with the lower end of the main shaft portion 23 via the tube portion 81. Because the lower end of the main shaft portion 23 does not rotate any more when the set screw 108 is blocked by the rod 103, the ring-shaped portion 82 is not rotated any more when the set screw 108 is blocked. Hence, the upper ring-shaped portion 83 rotates with respect to the lower ring-shaped portion 82 while the main shaft portion is twisted. By rotating the handle 3 until the upper visual mark 9b is aligned with the lower visual mark 9a, a predefined tightening torque is applied. Because of the gear unit 5, a final tightening of the set screw is possible even with a manual application of low tightening torque.

The tool may be preassembled or assembled before or during surgery.

The visual mark 9a can be applied when calibrating the tool.

The angle of 90° between the drive shaft 1 and the driven shaft 2 provides a convenient handling.

As shown in FIGS. 4 and 5, the torque flow is such that the torque is transmitted from the driven shaft to the set screw and is redirected by the end section 63 of the counter-holding portion. Therefore, no forces are conducted via the rod 103 back to the receiving portion 109, which could loosen the anchoring section in the bone.

The upper portion of a further embodiment of the tool is shown in FIGS. 15 and 16. The tool differs from the tool of the previous embodiment in that a preset torque adapter 90 is provided, which limits the applicable torque to a specific predefined value. The preset torque adapter 90 is arranged in a housing 4', which can be releasably connected to the main shaft portion 23 of the driven shaft. The preset torque adapter 90 has a shaft portion 91 which can be coupled to the main shaft portion 23 to transfer the torque. The preset torque adapter further has a recess 92 on the side opposite to the shaft portion 91 in which a shaft 53' engages. Shaft 53' is fixidly connected to the worm wheel 52 of the gear unit 5. The recess 92 may be a square recess, hexagon recess, or any other recess by means of which torque can be transferred from the shaft portion 53' to the torque adapter 90. The torque adapter 90 has in its interior a clutch mechanism (not shown) which has a defined release torque. For example, the clutch mechanism can be a slipping clutch. If the applied torque exceeds the predefined torque, the torque is no longer transferred from the shaft portion 53' via the torque adapter 90 to the main shaft portion 23.

As shown in FIGS. 15 and 16, the housing 4' also contains the gear unit 5. It may be closed by a closure 45 with or without an additional handle. Further, the housing 4' can be connected to the counter-holding portion 6 via a screw, a press fit, or any other connection 46. The whole unit including the gear unit and the torque adapter can be selectively connected instead of the housing with the gear unit and the display unit according to the previous embodiment.

As shown in FIG. 16, the housing 4' has a lower sleeve-shaped portion 400 that has an inner conically-shaped section 400a and the counter-holding portion 6 has at the free end of the main tube portion 62 an end portion 600 with an outer complementary conically-shaped portion 600a that is introduced into the sleeve-shaped portion 400 so that the housing 4' and the counter-holding portion 6 are connected at the conical portions by means of a friction fit. A nut element 700 is screwed onto the sleeve-shaped portion 400 to secure the parts against each other.

As shown in FIGS. 17, 18a and 18b a still further embodiment of the tool differs from the previous embodiments mainly by the type of connection between the housing 4' and the counter-holding portion 6. The housing 4' has a lower sleeve-like portion 401 with an outer thread 402 which cooperates with a corresponding inner thread of the nut member 700. The inner wall of the sleeve-shaped portion 401 comprises a plurality of coaxial recesses 403 like a Torx®-wrench that cooperates with a correspondingly-shaped end portion 601 of the counter-holding portion 600 to provide a positive-fit connection. Thereby, a safe connection is guaranteed even in the case of large torques to be transferred. Furthermore, the positive-fit connection is advantageous in view of a modular tool that allows the surgeon to easily exchange the components such as the counter-holding portion or the housing portion with gear. For example, the upper portion of the tool can be provided as several individual different upper portions comprising either different gear units and/or preset torque adapters and/or different display members. They can be selectively connected to the counter-holding portion. In a similar manner, different counter-holding portions that are used for different screws can be provided and selectively connected to the upper portion.

The embodiment shown in FIGS. 17, 18a and 18b has, for example, different handle portions 3' and 7' for the drive shaft and the counter-holding portion 6, respectively.

Various modifications of the tool are conceivable. The gear unit need not be a worm drive. It could also be realized by a planetary gear unit, in particular with coaxial drive shaft and driven shaft. Any other reduction gear unit may be used also.

The counter-holding portion and the tip portion may be exchanged such that the counter holding portion is at the center and the tip portion of the screw driver is surrounding it.

The counter-holding portion and the tip portion can be adapted in their shape to various shapes of receiving portions and locking elements.

What is claimed is:

1. A tool for use with a bone anchor, the tool comprising:
a tip portion configured to engage a locking element of the bone anchor;
a mechanism to apply torque to the tip portion, the mechanism comprising a drive shaft, a driven shaft and a gear unit comprising at least two gears, the gear unit configured to couple the drive shaft to the driven shaft;
wherein the drive shaft has a different axis than the driven shaft;
wherein the driven shaft comprises an engagement portion configured to releasably connect the driven shaft to the gear unit for torque transfer, the engagement portion being movable from a first position in which the entire gear unit is disconnected from the engagement portion of the driven shaft such that the driven shaft is released from the entire gear unit to a second position in which the entire gear unit is connected to the driven shaft at the engagement portion such that the gear unit can apply torque to drive the driven shaft; and
a counter-holding portion rotatable with respect to the tip portion.

2. The tool of claim 1, wherein the gear unit comprises a worm drive.

3. The tool of claim 2, wherein the gear unit is a reduction gear unit, wherein the gear reduction is in a range of approximately 3:1 to 10:1.

4. The tool of claim 2, wherein the tip portion is configured to releasably connect to the driven shaft.

5. The tool of claim 2, wherein the tip portion is one of a plurality of different tip portions, each of which is configured to be interchangeably connected to the driven shaft.

6. The tool of claim 1, wherein the counter-holding portion comprises an engagement portion configured to provide a positive fit connection with a receiving portion of the bone anchor.

7. The tool of claim 6, wherein the engagement portion of the counter-holding portion has two opposite flat surfaces.

8. The tool of claim 1, wherein the gear unit is a reduction gear unit, wherein the gear reduction is in a range of approximately 3:1 to 10:1.

9. The tool of claim 1, wherein the tip portion is configured to releasably connect to the driven shaft.

10. The tool of claim 1, wherein the drive shaft comprises a handle.

11. The tool according to claim 1, further comprising:
a counter-holding handle connected to the counter-holding portion; and
a drive shaft handle connected to the drive shaft,
wherein the drive shaft handle extends substantially perpendicular to the counter-holding handle.

12. The tool according to claim 1, wherein the gear unit comprises a drive gear and a driven gear, and wherein the driven shaft comprises an engagement portion configured to releasably connect the driven shaft to the driven gear.

13. A kit comprising a tool for use with at least one bone anchor, the at least one bone anchor comprising an anchoring section configured to be anchored to a bone, a receiving portion for receiving a rod, and a locking element configured to cooperate with the receiving portion to secure the rod to the receiving portion, wherein the tool comprises:
a plurality of tip portions, at least one tip portion of the plurality of tip portions configured to engage the locking element of the at least one bone anchor;
a mechanism to apply torque to the at least one tip portion, the mechanism comprising a drive shaft, a driven shaft and a gear unit, the gear unit configured to couple the drive shaft to the driven shaft; wherein the drive shaft has a different axis than the driven shaft;
a counter-holding portion rotatable with respect to the at least one tip portion and the counter-holding portion configured to provide a positive fit connection with the receiving portion to prevent rotation of the receiving portion relative to the counter-holding portion; and
a plug member comprising a resilient portion configured to interchangeably connect a respective one of the plurality of tip portions to the driven shaft.

14. The kit according to claim 13, further comprising the at least one bone anchor.

15. The kit according to claim 14, wherein the at least one tip portion comprises an engagement portion having a shape corresponding to a complementary engagement portion on the locking element of the at least one bone anchor in order to apply torque to the locking element.

16. A tool according to claim 1,
wherein the counter-holding portion is selectively exchangeable with another counter-holding portion,
wherein the mechanism to apply torque to the tip portion is selectively exchangeable with another mechanism to apply torque to the tip portion, and
wherein the tip portion is one of a plurality of different tip portions, each of which is configured to be interchangeably connected to the driven shaft.

17. A method of fastening a bone anchor with a tool,
wherein the tool comprises:
a tip portion for engaging a locking element of the bone anchor;
a mechanism to apply torque to the tip portion, the mechanism comprising a drive shaft and a driven shaft coupled by a gear unit,
wherein the drive shaft has a different axis than the driven shaft,
wherein the driven shaft comprises an engagement portion configured to releasably connect the driven shaft to the gear unit; and
a counter-holding portion rotatable with respect to the tip portion,
the method comprising:
selecting the bone anchor comprising a receiving portion and the locking element for fixation of a rod in the receiving portion;
inserting the bone anchor into a bone;
inserting the rod into the receiving portion of the bone anchor;
engaging the receiving portion with an engagement portion of the counter-holding portion;
inserting the driven shaft including the tip portion into the counter-holding portion;
mounting a housing onto the counter-holding portion, wherein the housing comprises a driving handle for rotating the drive shaft, the gear unit and a handle for holding the tool; and
rotating the drive shaft via the driving handle to screw in the locking element.

18. The method of claim 17, wherein the step of mounting the housing onto the counter-holding portion is performed before the steps of engaging the receiving portion with the engagement portion of the counter-holding portion and inserting the driven shaft including the tip portion into the counter-holding portion.

19. The method of claim 18, further comprising applying a predefined or set tightening torque.

20. The method of claim 17, further comprising applying a predefined or set tightening torque.

21. A tool for use with a bone anchor, the tool comprising:
a tip portion for engaging a locking element of the bone anchor;
a mechanism to apply torque to the tip portion, the mechanism comprising a drive shaft and a driven shaft coupled by a gear unit,
wherein the drive shaft has a different axis than the driven shaft,
a counter-holding portion rotatable with respect to the tip portion; and
a display member configured to indicate a value of the applied torque,
wherein the mechanism comprises a twistable element and the display member indicates a twisting thereof,
wherein the display member comprises a first portion connected to a first end of the twistable element and a second portion connected to a second end of the twistable element,
wherein the first portion and the second portion are rotatable against each other when the twistable element is twisted.

22. The tool of claim 21, wherein the gear unit is a reduction gear unit, wherein the gear reduction is in a range of approximately 3:1 to 10:1.

23. The tool of claim 21, wherein the tip portion is releasably connected to the driven shaft of the gear unit.

\* \* \* \* \*